(12) United States Patent
Menichetti et al.

(10) Patent No.: US 11,404,165 B2
(45) Date of Patent: Aug. 2, 2022

(54) FOODOME PLATFORM

(71) Applicant: Northeastern University, Boston, MA (US)

(72) Inventors: Giulia Menichetti, Boston, MA (US); Albert-Làszló Barábasi, Brookline, MA (US); Peter Ruppert, Chestnut Hill, MA (US)

(73) Assignee: Northeastern University, Boston, MA (US)

( * ) Notice: Subject to any disclaimer, the term of this patent is extended or adjusted under 35 U.S.C. 154(b) by 1002 days.

(21) Appl. No.: 15/939,946

(22) Filed: Mar. 29, 2018

(65) Prior Publication Data
US 2018/0286516 A1 Oct. 4, 2018

Related U.S. Application Data

(60) Provisional application No. 62/479,287, filed on Mar. 30, 2017.

(51) Int. Cl.
*G16H 50/30* (2018.01)
*G16H 50/50* (2018.01)
(Continued)

(52) U.S. Cl.
CPC ............. *G16H 50/30* (2018.01); *G16H 20/60* (2018.01); *G16H 50/50* (2018.01); *G16H 50/70* (2018.01)

(58) Field of Classification Search
USPC .............................................. 705/7.11–7.42
See application file for complete search history.

(56) References Cited

U.S. PATENT DOCUMENTS

| 2010/0070455 A1* | 3/2010 | Halperin | G16B 20/00 706/54 |
| 2010/0113892 A1* | 5/2010 | Kaput | G16B 20/20 600/301 |

(Continued)

OTHER PUBLICATIONS

Minkiewicz, et al., Internet Databases of the Properties, Enzymatic Reactions, and Metabolism of Small Molecules—Search Options and Applications in Food Science, International Journal of Molecular Sciences, 2016, pp. 1-24 (Year: 2016).*

(Continued)

*Primary Examiner* — Amber A Misiaszek
(74) *Attorney, Agent, or Firm* — Hamilton, Brook, Smith & Reynolds, P.C.

(57) ABSTRACT

The disclosed systems and methods provide a systematic approach to analyzing an individual's lifestyle factors (e.g., foods consumed by the individual) that contribute to the individual's current or potential for disease, and taking further action based on that analysis. One example embodiment is a machine learning system that includes a food composition layer, chemical compounds layer, and disease layer. The food composition layer provides representations of chemical compounds of foods consumed or to be consumed by the individual. The chemical compounds layer is coupled to the food composition layer by links and filters the representations of the chemical compounds based on genetic or metabolic information of the individual, resulting in representations of personalized filtered chemical compounds. The disease layer is coupled to the chemical compounds layer by links and associates a representation of a disease with representations of the personalized filtered chemical compounds based on a disease module for the disease.

22 Claims, 8 Drawing Sheets

(51) Int. Cl.
 *G16H 20/60* (2018.01)
 *G16H 50/70* (2018.01)

(56) References Cited

U.S. PATENT DOCUMENTS

| | | | |
|---|---|---|---|
| 2013/0151270 A1* | 6/2013 | Nova | G16H 20/60 705/2 |
| 2015/0168365 A1* | 6/2015 | Connor | G01N 33/02 356/402 |
| 2016/0232279 A1 | 8/2016 | Ghiassian et al. | |
| 2017/0199189 A1* | 7/2017 | Wade | G01N 33/56955 |

OTHER PUBLICATIONS

Vinayaham, et al. "Controllability analysis of the directed human protein interaction network identifies disease genes and drug targets", PNAS, May 3, 2016, 113 (18) 4976-4981—www.pnas.org/cgi/doi/10.1073/pnas.1603992113.

Ghiassian, et al. "A DIseAse MOdule Detection (DIAMOnD) Algorithm Derived from a Systematic Analysis of Connectivity Patterns of Disease Proteins in the Human Interactome", PLoS Comput Biol, Apr. 8, 2015, 11(4): e1004120.doi:10.1371/journal.pcbi.1004120.

Guney, et al. "Network-based in silico drug efficacy screening", Nature Communications, Feb. 1, 2016, DOI: 10.1038/ncomms10331 / www.nature.com/naturecommunications.

Menche, et al. "Uncovering disease-disease relationships through the incomplete human interactome", Science, Feb. 20, 2015, 347(6227): 1257601.doi:10.1126/science.1257601.

Liu, et al. "Controllability of complex networks", Nature, May 12, 2011, vol. 473, pp. 167-173.

\* cited by examiner

FOODOME PLATFORM

RELATED APPLICATION

This application claims the benefit of U.S. Provisional Application No. 62/479,287, filed on Mar. 30, 2017. The entire teachings of the above application are incorporated herein by reference.

BACKGROUND

The foods consumed by an individual can have a profound impact of the individual's health. Current technology, however, does not provide a mechanism for determining what effects particular foods have or are likely to have on a particular individual.

SUMMARY

The disclosed systems and methods provide a systematic approach to analyzing an individual's lifestyle factors (e.g., foods consumed by the individual) that contribute to the individual's current or potential for disease in order to accurately detect relationships between the individual's diet and disease.

One example embodiment is a machine learning system for determining associations between foods and diseases for an individual. The example system includes a food composition layer, chemical compounds layer, and disease layer. The food composition layer is configured to provide digital representations of chemical compounds of foods consumed or to be consumed by the individual. The chemical compounds layer is coupled to the food composition layer by links, and is configured to filter the digital representations of the chemical compounds of the foods consumed or to be consumed by the individual based on genetic and metabolic information of the individual, resulting in representations of personalized filtered chemical compounds. The disease layer is coupled to the chemical compounds layer by links, and is configured to associate a representation of a disease with representations of the personalized filtered chemical compounds based on a disease module for the disease. The disease module includes a digital model of the disease, which can include all disease-associated proteins and metabolites, together with their interactions. The links between successive layers are selected and weighted based on the foods consumed or to be consumed by the individual, the genetic information of the individual, the metabolic information of the individual, or a combination thereof. The links between successive layers and the weights of the links can be created or modified through machine learning based on patient training data.

The food composition layer can include a mapping between the foods consumed by the individual and chemical compounds included in the foods. The chemical compounds layer can include a mapping between the filtered chemical compounds and the genetic/metabolic information of the individual. The disease layer can include a mapping between the genetic/metabolic information of the individual and components of the disease module.

In some embodiments, the food composition layer can include a dish layer and an ingredients layer, in which case the ingredients layer can be coupled to the dish layer by links. Links between the dish layer and the ingredients layer can be determined based on known recipes for foods in the dish layer. The chemical compounds layer can be coupled to the ingredients layer by links, where the links between the ingredients layer and the chemical compounds layer can be determined based on information regarding chemical compounds included in ingredients.

Another example embodiment is a computer-implemented method of determining associations between foods and diseases for an individual. The example method includes determining digital representations of chemical compounds included in foods consumed or to be consumed by the individual, and filtering the digital representations of the chemical compounds of the foods based on genetic or metabolic information of the individual, resulting in representations of personalized filtered chemical compounds. The example method further includes determining representations of genetic components associated with the personalized filtered chemical compounds based on the genetic or metabolic information for the individual, and determining components of a disease module associated with the personalized filtered chemical compounds based on the representations of genetic components.

Another example embodiment is a computer-implemented method of personalizing nutrition for an individual. The example method includes determining digital representations of chemical compounds included in foods consumed or to be consumed by the individual, and filtering the digital representations of the chemical compounds of the foods based on genetic and metabolic information of the individual, resulting in representations of personalized filtered chemical compounds. The example method further includes determining representations of genetic components associated with the personalized filtered chemical compounds based on the genetic or metabolic information for the individual, and, based on the representations of genetic components and a disease module including a digital model of a disease, determining representations of certain chemical compounds affecting the disease for the individual. The example method may further include suggesting or creating foods for the individual to consume based on the representations of certain chemical compounds affecting the disease for the individual. In many embodiments, the genetic information of the individual can include a genome of the individual, and the metabolic information of the individual can include a metabolome of the individual.

Some embodiments can include tracking food consumed by the individual using a device ingested by the individual, where the device is configured to measure chemical compounds consumed by the individual. Other embodiments can include tracking food consumed or to be consumed by the individual by obtaining an image of the foods (e.g., with a camera of a mobile device) and processing the image to determine what foods are present in the image and what chemical compounds are present in the foods.

Determining digital representations of chemical compounds included in foods consumed or to be consumed by the individual can include determining the digital representations of chemical compounds based on known recipes for the foods, which can include determining ingredients that are commonly found in the foods based on the known recipes for the foods and determining chemical compounds corresponding to the ingredients or cooking methods.

Filtering the digital representations of the chemical compounds based on genetic or metabolic information of the individual can include referencing information regarding how the chemical compounds are related to a human genome or metabalome for the individual.

BRIEF DESCRIPTION OF THE DRAWINGS

The foregoing will be apparent from the following more particular description of example embodiments, as illus

DETAILED DESCRIPTION

A description of example embodiments follows.

Disclosed is a platform and method that identifies chemical compounds, or a mixture of chemical compounds, that have a critical impact on the metabolism, health, performance, and disease resistance of humans and animals. The resulting personalized chemical compounds exposure profiles (PCCEP) allow for a detailed investigation of the chemical/molecular roots of a disease state of an individual, in contrast to conventional ingredient-based diet profiles and analysis methods. The PCCEPs offer the possibility of providing direct feedback on altering eating patterns to maximize health and performance benefits and minimize disease risk. Such a platform and method can be referred to as a "foodome" platform.

One example embodiment is a platform and method that breaks down food dish information collected on a mobile device (e.g., from pictures, text, or voice recorded data). In one example embodiment, the foodome platform may incorporate or rely upon a mobile software platform. If based on pictures, known image processing techniques can be used to determine what foods are present in the pictures. If based on voice recorded data, known sound processing techniques can be used to determine what foods are present in the voice recorded data. The platform identifies chemical compounds, or a mixture of chemical compounds, that are present in the food dish and that impact the metabolomics or regulatory reactions of an individual's body. Overall, the foodome platform provides a quantitative model and procedure to break a dish into its ingredients.

The foodome platform does not stop at the ingredient level. It allows further breakdown of food into chemical compounds and mixtures of chemical compounds for a significantly better optimization process. The foodome platform and method allows for a systematic quantification of the heterogeneity of a diet for subjects with different genetic and metabolic profiles. Novel chemical compound exposure levels connected to a larger set of genes and metabolites allow for an optimized diet tailored to an individual's genomic profile.

The foodome platform can work with the latest, scientifically proven, state-of-the art datasets to provide a fact-based recommendation engine for future food selections optimized for an individual's physiological characteristics. The foodome platform can be used to track the food intake of individuals for sufficiently long period(s) to identify their individualized intake patterns and to break down the chemical palette that contributes to disease development. Based on these data inputs, the platform can provide recommendations for optimized and disease-based personalized diet plans for purchase and consumption.

The resulting personalized chemical compounds exposure profiles (PCCEP) provide a quantitative, chemical compound-wide description of the exposure level of an individual. PCCEPs can be used to construct novel chemical compound-based foods or diets for disease states. PCCEPs can be used to provide recommendations of foods to avoid or to consume in order to maximize the benefits of healthy nutrients and minimize health risks.

The foodome platform, which creates PCCEPs, can be used, for example, to (1) measure chemical compounds in patients with disease and control subjects, (2) provide a personalized food diary for collecting data on an individual's chemical exposure profile and providing feedback, (3) identify novel chemical compound relationships with metabolomics or regulatory reactions, and (4) create the fundamentals of a personalized chemical-genome diet. As a result, food production and agricultural GMO developers can optimize product portfolios based on chemical compounds and contribute to healthcare therapies. Insurance companies can monitor food intake based on, for example, a phone-based application input and classify and assess individual plans. Hospital, prison, and school food services can be optimized for individual meal plans.

Figure 1:
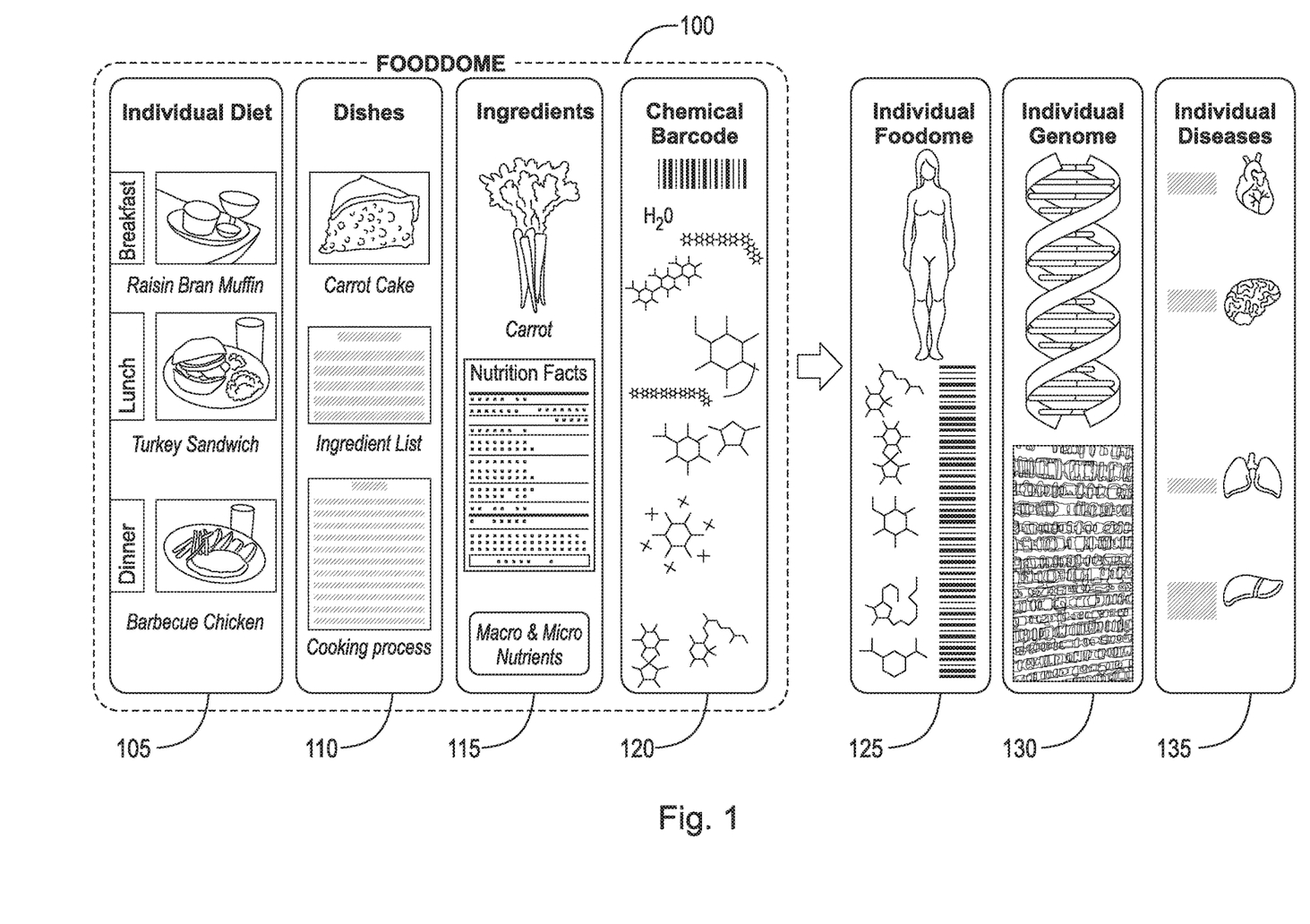
- FIG. 1 is a schematic diagram illustrating determining associations between foods and diseases for an individual, according to an example embodiment.

FIG. 1 is a schematic diagram illustrating associations between foods and diseases for an individual. FIG. 1 depicts a graphical representation of an example implementation of the foodome platform 100. A given individual has an given diet 105 compared to other individuals. That diet 105 includes a number of food dishes 110, each of which is made up of a number of ingredients 115. These ingredients 115 are made up of a number of chemical compounds 120.

The foodome platform 100 can track with high accuracy the food intake of individuals for sufficiently long periods to identify their individualized chemical palette. The foodome platform can identify the consumed ingredients 115 and then break the ingredients into their chemical constituents 120, enabling assembly of an encoded individualized foodome 125 that captures the chemical palette to which an individual is exposed. The foodome platform can be used to identify new and precise chemical risk factors associated with foods for certain diseases. The foodome platform can be used to search for cellular mechanics through which these chemicals affect diseases, and to offer recommendations of foods to consume or avoid in order to change or balance the chemical profile of an individual. This can be accomplished by determining associations among the chemical compounds 120 with disease models 135 based on the individual's genetic or metabolic information 130 (e.g., genome or metabolome).

As referred to herein, a "genome" is a complete set of genes or genetic material that are present in an individual (e.g., the complete list of the nucleotides that make up the chromosomes of an individual). As referred to herein, a "metabolome" is a complete set of metabolites that are present within an individual. A metabolome reflects the interaction between an individual's genome and its environment. The Human Metabolome Database, for example, is a freely available, open-access database containing information on thousands of metabolites that have been identified. Metabolites can be measured using a number of different technologies including Nuclear Magnetic Resonance (NMR) spectroscopy and mass spectrometry.

Figure 2:
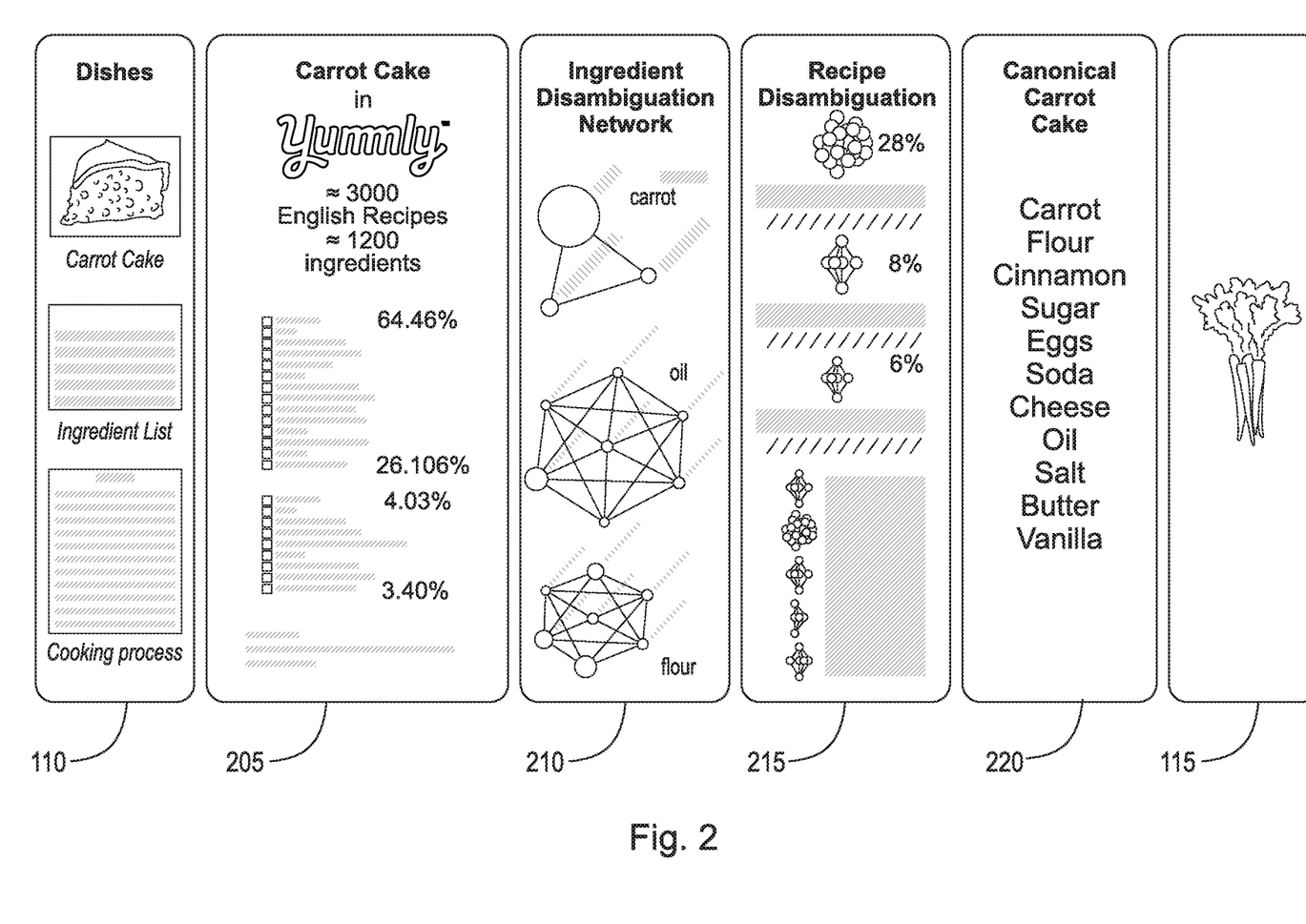
FIG. 2 is a schematic diagram illustrating determining ingredients likely to be included in a food dish, according to an example embodiment.

FIG. 2 is a schematic diagram illustrating ingredients likely to be included in a food dish. For a given dish 110 consumed by an individual, known recipes 205 can be used to determine the ingredients 115 typically found in the given dish 110. As depicted in FIG. 2, known recipes 205 can be referenced to determine a large number of ingredients 210 that are commonly found in an example dish of a carrot cake 110. The large number of ingredients 210 can be reduced through a process of ingredient disambiguation. For example, "shredded carrots" and "grated carrots" can be simplified to be "carrots." Further, the large number of recipes 215 can be reduced to a most common recipe 220 through a process of recipe disambiguation.

Figure 3:
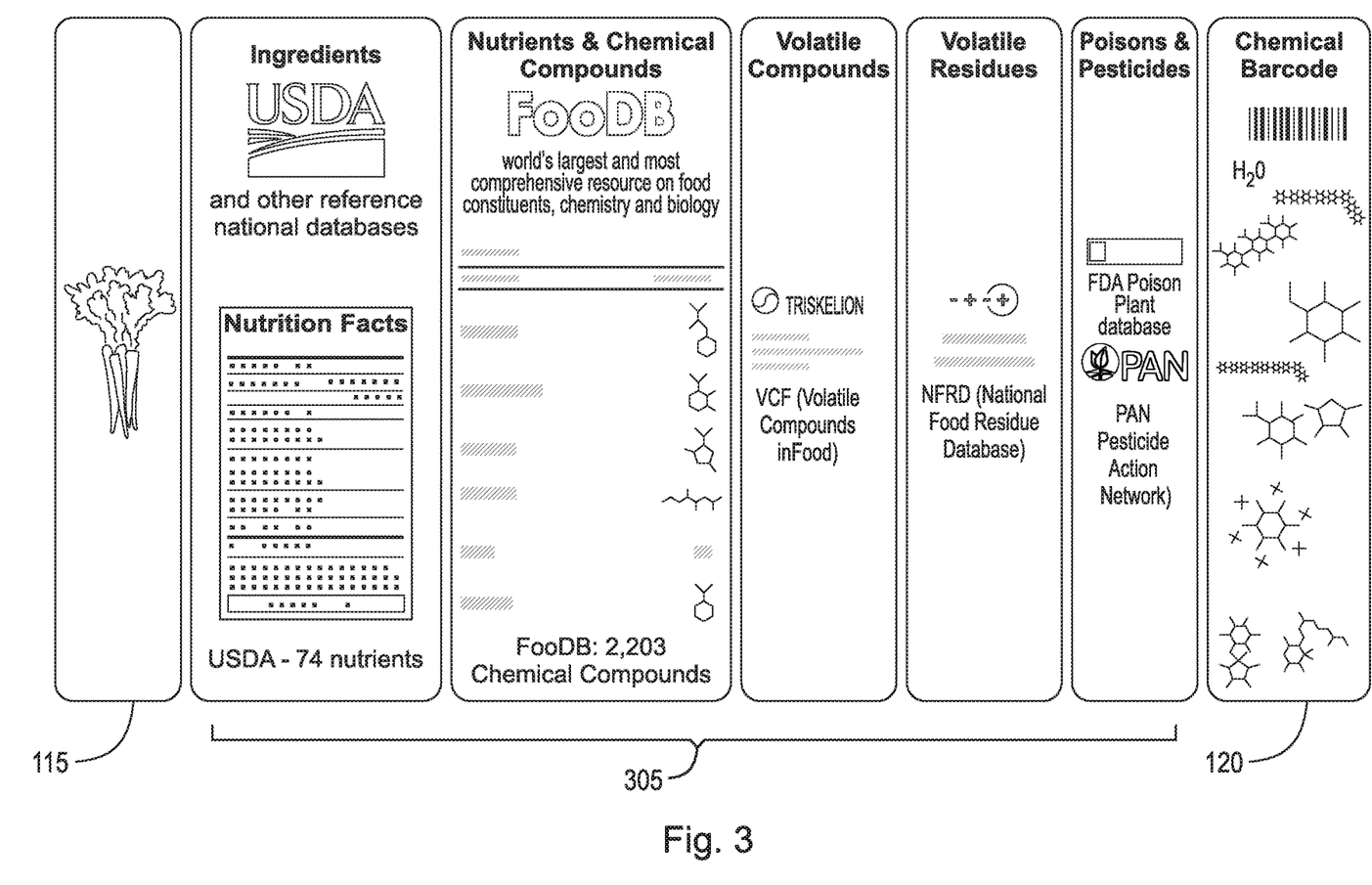
FIG. 3 is a schematic diagram illustrating determining chemical compounds of an ingredient, according to an example embodiment.

FIG. 3 is a schematic diagram illustrating chemical compounds of an ingredient. For a given ingredient 115 (e.g., carrot), various resources, such as, for example, United States Department of Agriculture data or other databases such as The Food. Database (FooDB), Volitile Compounds in Food (VCF). National Food Residue Database (NFDB), and Pesticide Action Network (PAN), can be referenced to determine the chemical compounds 120 that make up the ingredient. Just one ingredient 115 can be made up of thousands of chemical compounds 120.

Figure 4:
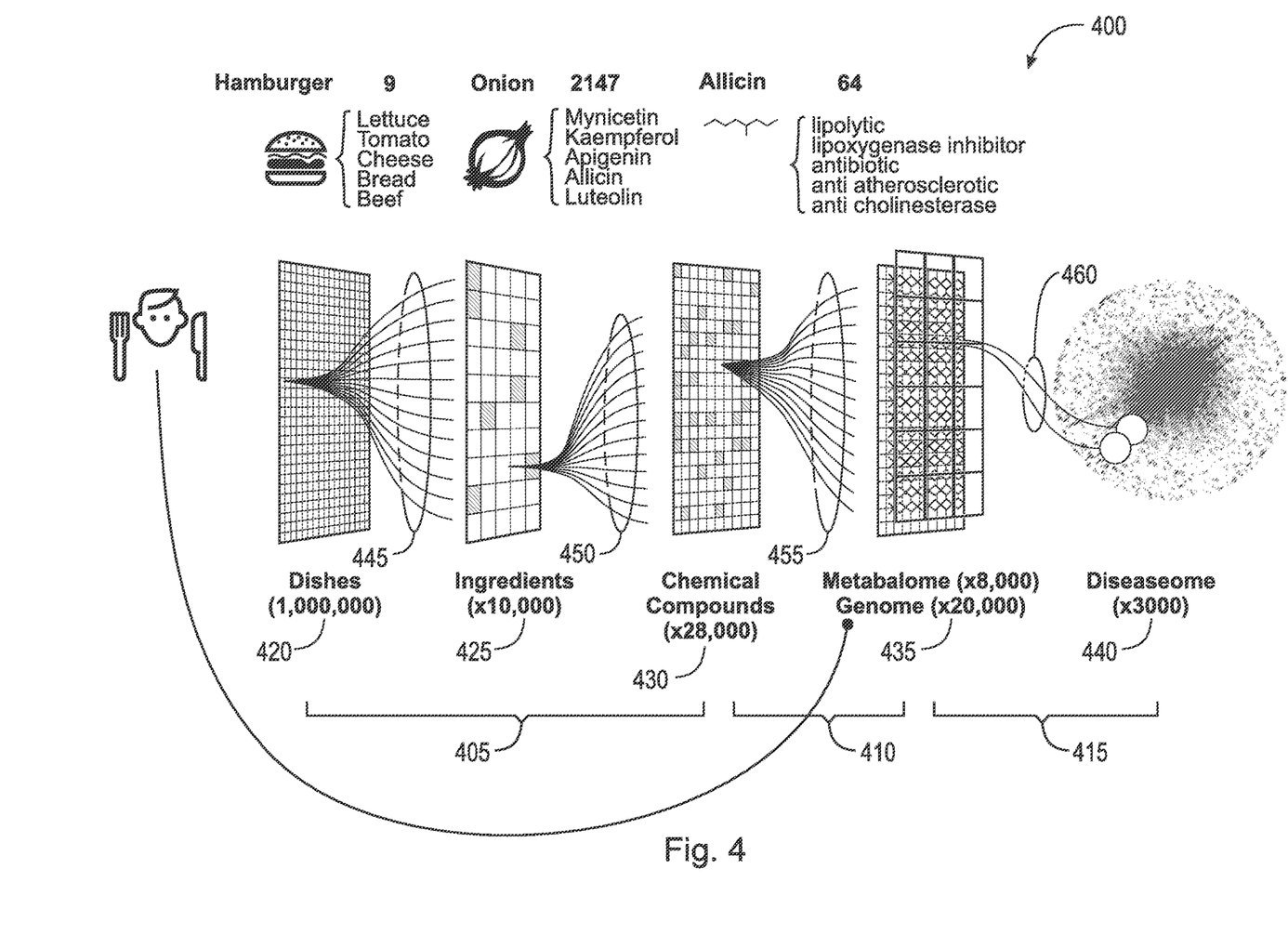
FIG. 4 is a schematic diagram illustrating determining associations between foods and diseases for an individual, according to an example embodiment.

FIG. 4 is a schematic diagram illustrating a system 400 for determining associations between foods and diseases for an individual, according to an example embodiment. The system can be organized into layers. The example system 400 includes a food composition layer 405, chemical compounds layer 410, and disease layer 415. The food composition layer 405 is configured to provide digital representations of chemical compounds 430 of foods 420 consumed or to be consumed by the individual. The chemical compounds layer 410 is coupled to the food composition layer 405 by links, and is configured to filter the digital representations of the chemical compounds 430 of the foods 420 consumed or to be consumed by the individual based on genetic/metabolic information 435 of the individual, resulting in representations of personalized filtered chemical compounds. The disease layer 415 is coupled to the chemical compounds layer 410 by links, and is configured to associate a representation of a disease with representations of the personalized filtered chemical compounds based on a disease module 440 for the disease. The disease module 440 includes a digital model of the disease and represents proteins within a protein network that are associated with the disease, and metabolites binding with proteins. Such proteins associated with a disease may be referred to as a disease cluster or disease module. As used herein, the disease module can be a disease module as disclosed in U.S. Patent Publication No. 2016/0232279, the entirety of which is incorporated herein by reference. The system can obtain data from external sources for improved details on, for example, ingredients, chemical compounds, metabolomes, genomes, and diseasomes.

As in the example system 400 illustrated in FIG. 4, the food composition layer can be broken down into dishes 420, ingredients 425, and chemical compounds 430. As shown, links 445 can be created between dishes 420 and ingredients 425, representing that certain ingredients make up a given dish. Links 450 can also be created between ingredients 425 and chemical compounds 430, representing that certain chemical compounds make up a given ingredient. For example, a hamburger often includes onion as an ingredient, which includes the chemical compound of allicin, for example.

The chemical compounds layer 410 can be broken down into chemical compounds 430 and a representation of the individual's genetic or metabolic information 435 (e.g., genome or metabalome). The chemical compounds layer 410 filters digital representations of the chemical compounds 430 based on the individual's genetic/metabolic information 435, resulting in representations of personalized filtered chemical compounds 455. For example, the chemical compound of allicin can affect lipolysis in different ways in different individuals based on the genetic makeup of the individuals.

The disease layer 415 can be broken down into the individual's genetic/metabolic information 435 and a disease module 440 for a disease. Links 460 can be created between proteins of the disease module 440 and the individual's genetic/metabolic information 435. The disease layer 415 associates a representation of the disease with representations of the personalized filtered chemical compounds 455 based on a disease module 440 for the disease and the individual's genetic/metabolic information 435. For example, if lipolysis has a certain effect on heart disease, the chemical compound of allicin may have a certain positive or negative effect on heart disease for a certain individual.

As shown in FIG. 4, due to the extremely large number of combinations of dishes, ingredients, chemical compounds, genetic information, metabolic information, and disease models, the example system lends itself to implementation on a computerized system, as manual implementation would be extremely impractical if not impossible. The filtering performed by the chemical compounds layer 410 reduces, based on the individual's genetic/metabolic information 435, the digital representations of the chemical compounds 430 to a manageable amount. Otherwise, the massive amount of data could be too much even for a computer to process efficiently. This process can be thought of as using an individual's genome/metabotome as a filter to focus on certain chemical compounds for a given disease. The resulting personalized filtered chemical compounds 455 are unique to the individual.

The links between the layers can be selected and weighted based on the foods consumed or to be consumed by the individual, the genetic information of the individual, the metabolic information of the individual, or a combination thereof. The links between successive layers and the weights of the links can be created or modified through machine learning trained with patient data. For example, the links between the chemical compounds layer 410 and the disease layer 415 can be determined using machine learning based on a large amount of patient training data.

Figure 5:
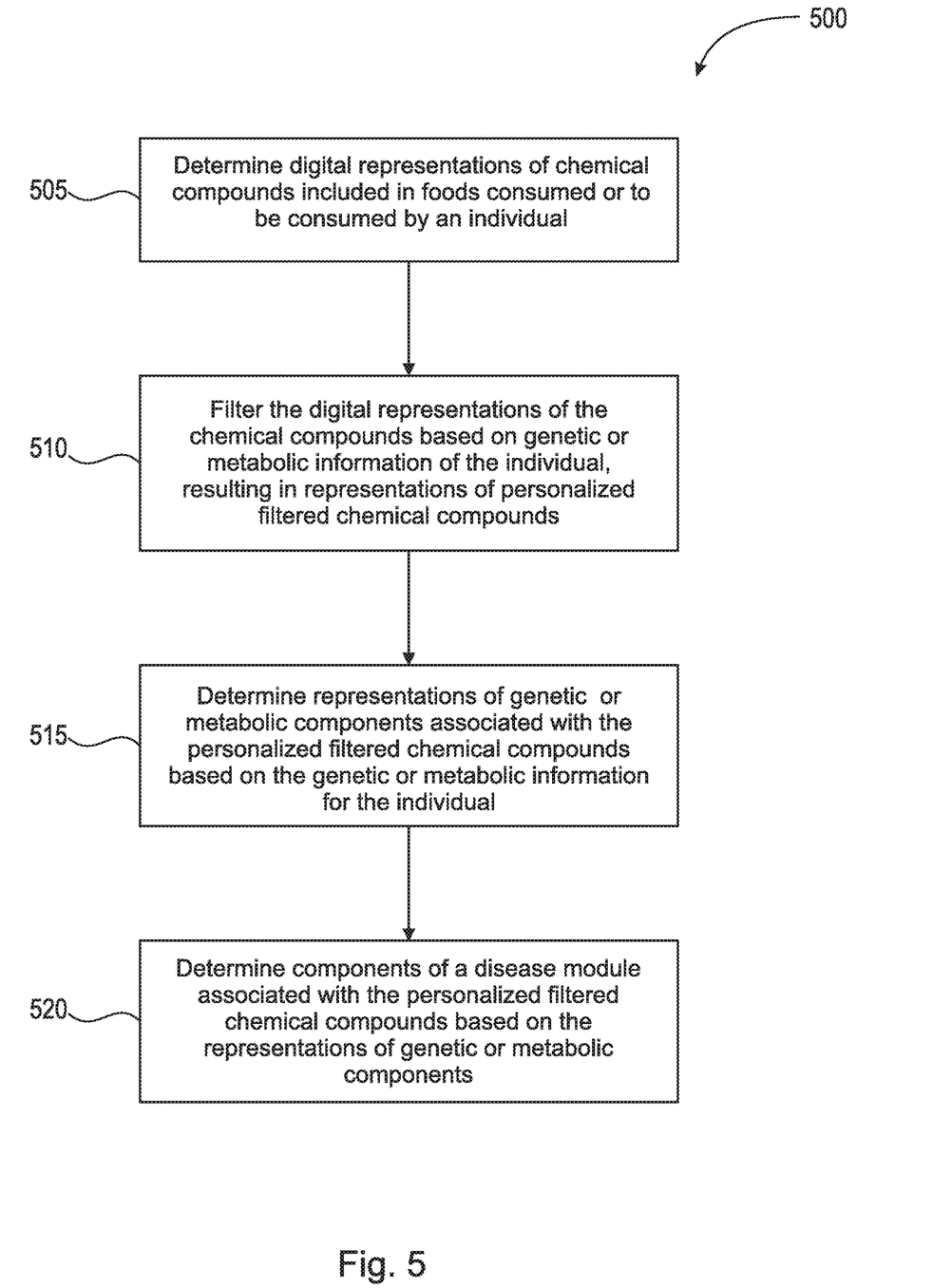
FIG. 5 is a flow diagram illustrating determining associations between foods and diseases for an individual, according to an example embodiment.

FIG. 5 is a flow diagram illustrating a method 500 of determining associations between foods and diseases for an individual, according to an example embodiment. The example method 500 includes determining 505 digital representations of chemical compounds included in foods consumed or to be consumed by the individual, and filtering 510 the digital representations of the chemical compounds of the foods based on genetic/metabolic information of the individual, resulting in representations of personalized filtered chemical compounds. The example method 500 further includes determining 515 representations of genetic components associated with the personalized filtered chemical compounds based on the genetic or metabolic information for the individual, and determining 520 components of a disease module associated with the personalized filtered chemical compounds based on the representations of genetic components.

Figure 6:
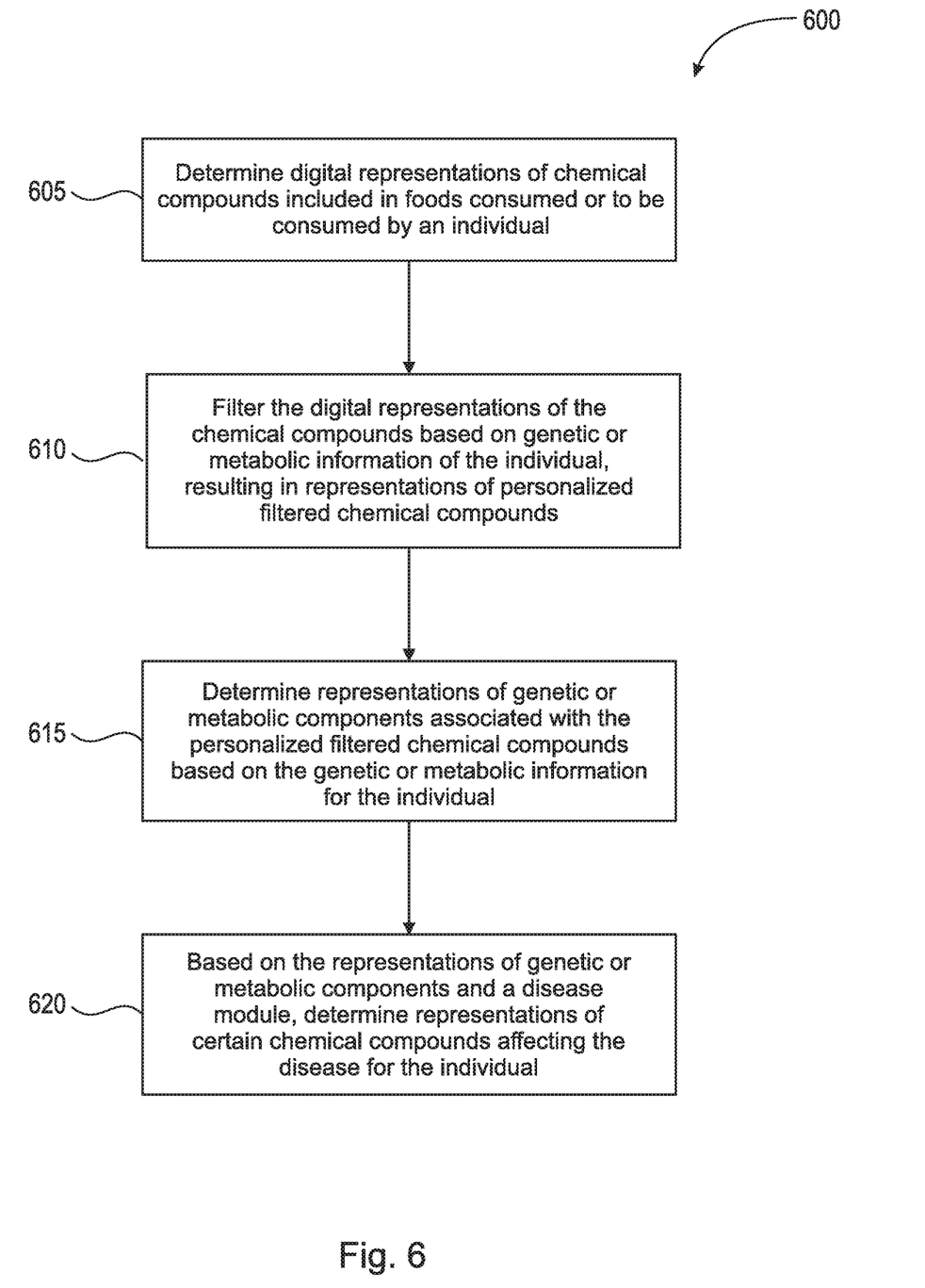
FIG. 6 is a flow diagram illustrating personalizing nutrition for an individual, according to an example embodiment.

FIG. 6 is a flow diagram illustrating a method 600 of personalizing nutrition for an individual, according to an example embodiment. The example method 600 includes determining 605 digital representations of chemical compounds included in foods consumed or to be consumed by the individual, and filtering 610 the digital representations of the chemical compounds of the foods based on genetic/metabolic information of the individual, resulting in representations of personalized filtered chemical compounds. The example method 600 further includes determining 615 representations of genetic components associated with the personalized filtered chemical compounds based on the genetic or metabolic information for the individual, and, based on the representations of genetic components and a disease module including a digital model of a disease, determining 620 representations of certain chemical compounds affecting the disease for the individual. Foods for consumption by the individual can be suggested or created based on the representations of certain chemical compounds affecting the disease for the individual. For example, with reference to FIG. 4 above, if the chemical compound of allicin is determined to have a positive effect on heart disease for a certain individual, the individual can be provided with a recommendation to consume more onion.

Figure 7:
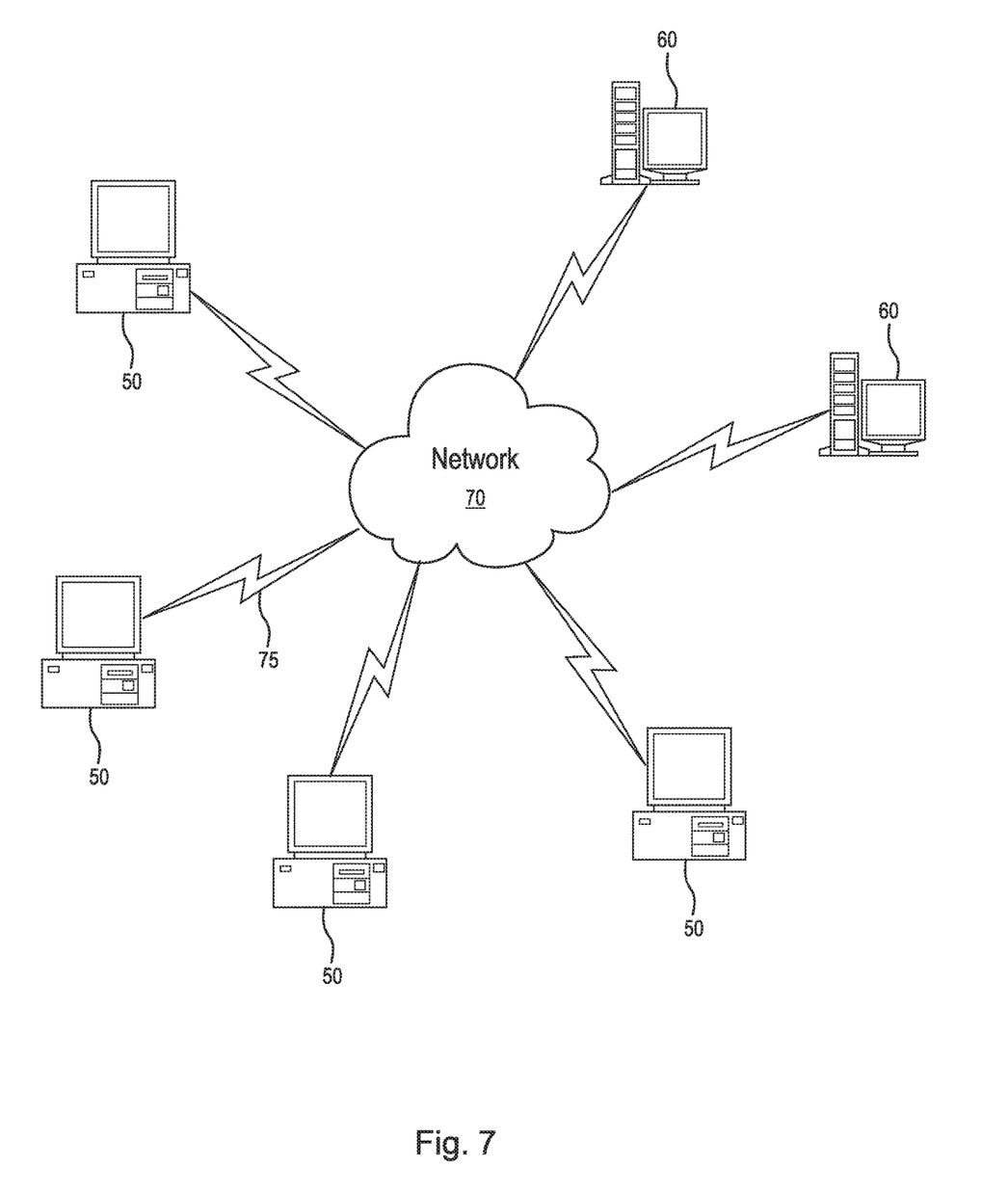
FIG. 7 is a schematic view of a computer network environment in which the example embodiments presented herein may be implemented.

FIG. 7 illustrates a computer network or similar digital processing environment in which the present embodiments may be implemented. Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/computer network architectures are suitable. In the context of such a network, a subscription-based service can be implemented on a server, for example, where the connected devices can provide to the service personalized data used by the example systems and methods disclosed herein to determine the associations and personalized nutrition information (e.g., foods to be consumed by a particular individual).

Figure 8:
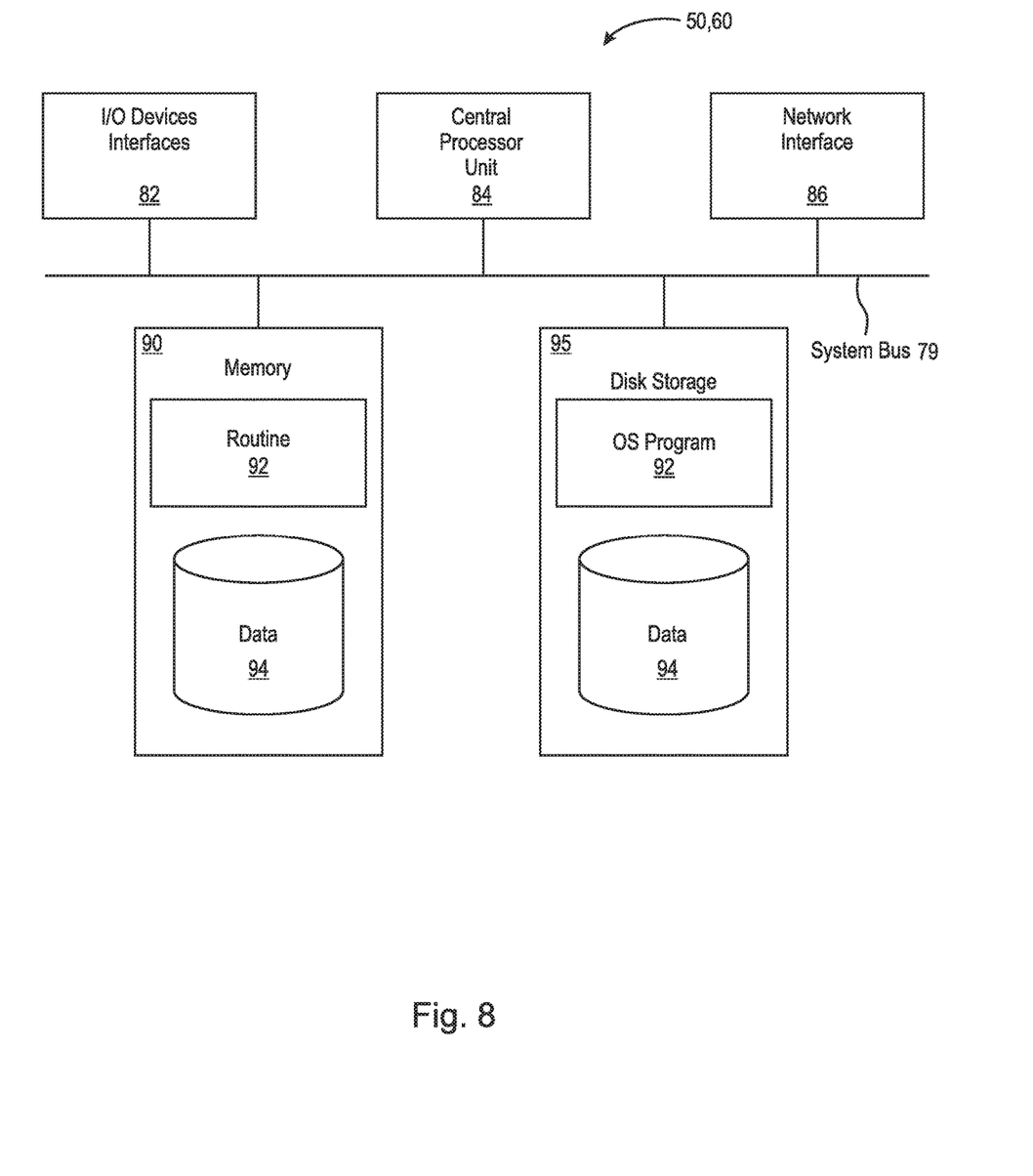
FIG. 8 is a block diagram illustrating an example computer node of the network of FIG. 7.

FIG. 8 is a diagram of the internal structure of a computer e.g., client processor/device 50 or server computers 60) in the computer system of FIG. 7. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, and network ports) that enables the transfer of information between the elements. Attached to system bus 79 is I/O device interface 82 for connecting various input and output devices (e.g., keyboard, mouse, displays, printers, and speakers) to the computer 50, 60. Network interface 86 allows the computer to connect to various other devices attached to a network (e.g., network 70 of FIG. 7). Memory 90 provides volatile storage for computer software instructions 92 and data 94 used to implement many embodiments (e.g., system 400 and methods 500 and 600). Disk storage 95 provides non-volatile storage for computer software instructions 92 and data 94 used to implement many embodiments. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, and tapes) that provides at least a portion of the software instructions for the system. Computer program product 92 can be installed by any suitable software installation procedure, as is well known in the art. In another embodiment, at least a portion of the software instructions may also be downloaded over a cable, communication and/or wireless connection. In other embodiments, the programs are a computer program propagated signal product 75 (FIG. 7) embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the routines/program 92.

In alternative embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product. Generally speaking, the term "carrier medium" or transient carrier encompasses the foregoing transient signals, propagated signals, propagated medium, storage medium and the like. In other embodiments, the program product 92 may be implemented as Software as a Service (SaaS), or other installation or communication supporting end-users.

While example embodiments have been particularly shown and described, it will be understood by those skilled in the art that various changes in form and details may be made therein without departing from the scope of the embodiments encompassed by the appended claims.

What is claimed is:

1. A machine learning system for determining associations between foods and diseases for an individual and providing a personalized exposure profile for the individual, the system comprising:

A database;

A processor;

a food composition layer configured to provide digital representations of chemical compounds of foods consumed or to be consumed by the individual;

a chemical compounds layer, coupled to the food composition layer by links, configured to filter the digital representations of the chemical compounds of the foods consumed or to be consumed by the individual based on genetic or metabolic information of the individual, resulting in representations of personalized filtered chemical compounds, the representations of personalized filtered chemical compounds being a reduced set of chemical compound representations to facilitate efficient processing; and a disease layer, coupled to the chemical compounds layer by links, configured to associate a representation of a disease with representations of the personalized filtered chemical compounds based on a disease module for the disease, the disease module including a digital model of the disease;

wherein the links between successive layers are selected and weighted using, at least in part, machine learning based on the foods consumed or to be consumed by the individual, the genetic information of the individual, the metabolic information of the individual, or a combination thereof, the system providing an output of a personalized exposure profile for the individual based on the associated representations of the disease and personalized filtered chemical compounds.

2. A machine learning system as in claim 1 wherein:
the food composition layer includes a mapping between the foods consumed by the individual and chemical compounds included in the foods;
the chemical compounds layer includes a mapping between the filtered chemical compounds and the genetic or metabolic information of the individual; and
the disease layer includes a mapping between the genetic or metabolic information of the individual and components of the disease module.

3. A machine learning system as in claim 1 wherein the genetic information of the individual includes a genome of the individual, the metabolic information of the individual includes a metabolome of the individual.

4. A machine learning system as in claim 1 wherein the links between successive layers and the weights of the links are created or modified through machine learning.

5. A machine learning system as in claim 1 wherein machine learning uses a neural network trained using patient data.

6. A machine learning system as in claim 1 wherein the food composition layer includes a dish layer and an ingredients layer, the ingredients layer being coupled to the dish layer by links.

7. A machine learning system as in claim 6 wherein the links between the dish layer and the ingredients layer are determined based on known recipes for foods in the dish layer.

8. A machine learning system as in claim 6 wherein the chemical compounds layer is coupled to the ingredients layer by links, the links between the ingredients layer and the chemical compounds layer being determined based on information regarding chemical compounds included in ingredients.

9. A machine learning system as in claim 1 wherein the links between the chemical compounds layer and the disease layer are determined using machine learning based on patient training data.

10. A computer-implemented method of determining associations between foods and diseases for an individual and providing a personalized exposure profile for the individual, the method comprising:
determining digital representations of chemical compounds included in foods consumed or to be consumed by the individual;

filtering the digital representations of the chemical compounds of the foods consumed or to be consumed by the individual based on genetic or metabolic information of the individual, resulting in representations of personalized filtered chemical compounds, the representations of personalized filtered chemical compounds being a reduced set of chemical compound representations to facilitate efficient processing;

determining representations of genetic components associated with the personalized filtered chemical compounds based on the genetic or metabolic information for the individual;

determining components of a disease module associated with the personalized filtered chemical compounds based on the representations of genetic components, the disease module including a digital model of the disease; and outputting a personalized exposure profile for the individual based on the determined components of the disease module, wherein determining components of the disease module includes selecting and weighing links among the representations of the personalized filtered chemical compounds and genetic components using, at least in part, machine learning.

11. A computer-implemented method as in claim 10 further comprising tracking food consumed by the individual using a device ingested by the individual, the device configured to measure chemical compounds consumed by the individual.

12. A computer-implemented method as in claim 10 further comprising tracking food consumed or to be consumed by the individual by obtaining an image of the foods and processing the image to determine what foods are present in the image and what chemical compounds are present in the foods.

13. A computer-implemented method as in claim 10 wherein determining digital representations of chemical compounds included in foods consumed or to be consumed by the individual includes determining the digital representations of chemical compounds based on known recipes for the foods.

14. A computer-implemented method as in claim 13 wherein determining the digital representations of chemical compounds based on known recipes for the foods includes determining ingredients commonly found in the foods based on the known recipes for the foods and determining chemical compounds corresponding to the ingredients.

15. A computer-implemented method as in claim 10 wherein filtering the digital representations of the chemical compounds based on genetic or metabolic information of the individual includes referencing information regarding how the chemical compounds are related to a human genome or metabalome for the individual.

16. A computer-implemented method of personalizing nutrition for an individual, the method comprising:
determining digital representations of chemical compounds included in foods consumed or to be consumed by the individual;
filtering the digital representations of the chemical compounds of the foods consumed or to be consumed by the individual based on genetic or metabolic information of the individual, resulting in representations of personalized filtered chemical compounds, the representations of personalized filtered chemical compounds being a reduced set of chemical compound representations to facilitate efficient processing;

determining representations of genetic components associated with the personalized filtered chemical compounds based on the genetic or metabolic information for the individual;

based on the representations of genetic components and a disease module including a digital model of a disease, determining representations of certain chemical compounds affecting the disease for the individual; and outputting a personalized exposure profile for the individual based on the determined components of the disease module, wherein determining representations of certain chemical compounds affecting the disease for the individual includes selecting and weighing links among the representations of the personalized filtered chemical compounds and genetic components using, at least in part, machine learning.

17. A computer-implemented method as in claim 16 further comprising suggesting or creating foods for the individual to consume based on the representations of certain chemical compounds affecting the disease for the individual.

18. A computer-implemented method as in claim 16 further comprising tracking food consumed by the individual using a device ingested by the individual, the device configured to measure chemical compounds consumed by the individual.

19. A computer-implemented method as in claim 16 further comprising tracking food consumed or to be consumed by the individual by obtaining an image of the foods and processing the image to determine what foods are present in the image and what chemical compounds are present in the foods.

20. A computer-implemented method as in claim 16 wherein determining digital representations of chemical compounds included in foods consumed or to be consumed by the individual includes determining the digital representations of chemical compounds based on known recipes for the foods.

21. A computer-implemented method as in claim 20 wherein determining the digital representations of chemical compounds based on known recipes for the foods includes determining ingredients commonly found in the foods based on the known recipes for the foods and determining chemical compounds corresponding to the ingredients.

22. A computer-implemented method as in claim 16 wherein filtering the digital representations of the chemical compounds based on genetic or metabolic information of the individual includes referencing information regarding how the chemical compounds are related to a human genome or metabalome for the individual.

* * * * *

UNITED STATES PATENT AND TRADEMARK OFFICE
CERTIFICATE OF CORRECTION

PATENT NO. : 11,404,165 B2  
APPLICATION NO. : 15/939946  
DATED : August 2, 2022  
INVENTOR(S) : Giulia Menichetti, Albert-László Barábasi and Peter Ruppert Page 1 of 1

It is certified that error appears in the above-identified patent and that said Letters Patent is hereby corrected as shown below:

In the Claims

In Claim 1, Column 8, Line 58, delete "A database;" and insert -- a database; --.

In Claim 1, Column 8, Line 59, delete "A processor;" and insert -- a processor; --.

Signed and Sealed this
Twenty-fourth Day of October, 2023

Katherine Kelly Vidal
*Director of the United States Patent and Trademark Office*